United States Patent [19]

Mannara

[11] 4,003,971
[45] Jan. 18, 1977

[54] PRODUCTION OF PARTICLES FOR INCORPORATION IN DENTIFRICES

[75] Inventor: Giuseppe Mannara, Rome, Italy

[73] Assignee: Colgate-Palmolive Company, New York, N.Y.

[22] Filed: Nov. 4, 1974

[21] Appl. No.: 520,665

[30] Foreign Application Priority Data

Nov. 16, 1973 Italy .................. 53749/73

[52] U.S. Cl. .................................................. 264/9
[51] Int. Cl.² .......................................... B01J 2/06
[58] Field of Search ............... 264/5, 9; 424/49, 52

[56] References Cited

UNITED STATES PATENTS

| | | | |
|---|---|---|---|
| 2,751,328 | 6/1956 | Sanders | 424/49 |
| 3,711,604 | 1/1973 | Colodney et al. | 424/52 |
| 3,728,446 | 4/1973 | Roberts et al. | 424/49 |

*Primary Examiner*—Robert F. White
*Assistant Examiner*—James R. Hall
*Attorney, Agent, or Firm*—Robert L. Stone; Murray M. Grill; Herbert S. Sylvester

[57] ABSTRACT

Dentifrice speckles of substantially uniform shape and size are made by agitating the material of such speckles (binder plus dentifrice component) in a liquid dispersing medium at a temperature at which the binder is liquid but undissolved and unemulsified in the dispersing medium, and cooling the dispersion to a temperature below the solidification point of the speckling material so as to solidify it into speckles of desired size. Such speckles may be separated from the dispersing medium or may remain in it and be utilized with it. Preferably the speckles are incorporated in dentifrices and contain dentifrice components desirably maintained separate from the rest of the dentifrice. Also included within the invention described are the speckles and dentifrices containing them.

9 Claims, No Drawings

PRODUCTION OF PARTICLES FOR INCORPORATION IN DENTIFRICES

The invention relates to an improved process for obtaining speckles for paste or powder dentifrice compositions and, more particularly, to a process for obtaining speckles of improved uniformity in size and shape, and to dentifrices containing them.

It is known to prepare speckled macroscopic visible particles for oral paste or powder dentifrice compositions, which speckles may contain, in addition to organic binder, one or more functional and/or aesthetic components of the dentifrice. The incorporation of speckles into such dentifrices, in addition to providing an attractive appearance, has additional advantages when a functional component or "active" ingredients of a dentifrice is present in the speckling material. Thus, functional components, when homogeneously distributed through the dentifrice, can be reduced in effectiveness or tend to be reactive with other functional dentifrice components, particularly on aging. However, their inclusion as speckles tends to keep them isolated from other ingredients and permits greater latitude in formulations of dentifrice compositions. The additions of these functional ingredients to the dentifrice can also be better controlled when these active agents are bound in speckling material and their presence is then often also visually evident. The incorporation of functional components into the speckles provides satisfactory stability or integrity of the component until release in use, that is, on toothbrushing, said speckles, if of a lipophilic material in an aqueous base, break up and may become emulsified in the hydrophilic materials so as to release the desired effect of the functional ingredient incorporated in the speckling material.

Prior art procedures for preparing particles for incorporation in dentifrices, hereafter called speckles, have had several serious disadvantages connected with obtaining the speckles in desired uniform sizes and shapes. Generally, the speckles have been prepared by melting a physiologically acceptable organic binder, such as a thermoplastic resin, wax or high molecular weight ester, e.g., glyceryl tristearate, and, if desired, mixing or blending with it a functional and/or aesthetic dentifrice component. One prior art method of converting the resultant speckling mass into solid particulate form has been to melt a mix, then cool it to solidify the binder and then to grind the solidified mass to particular form. The resultant particles, however, are somewhat irregular in appearance and size. Only by tedious, costly screening or sieving can particles of uniform size, desirably in the range of about 0.05 to 1 mm., be obtained. Such screening or sieving generally results in losses of speckling material, for example, losses of as much as 50% or more of the speckling material which is originally charged to the screening or sieving process, but which is of a particle size either too great or too small to be acceptable. Furthermore, the resultant speckles, while having a desired uniformity of size nevertheless are of less attractive irregular shapes. In order to overcome the disadvantages of the aforementioned or standard grinding or size reduction methods other comminution procedures, such as spray drying, spray cooling, extrusion, pressing, and cutting techniques have been suggested or applied to the problem of obtaining dentifrice speckles. However, spray cooling, while providing speckles of improved uniformity of shape nevertheless entails disadvantageous sieving or screening of the cooled particulate speckling material with the aforementioned losses. The other techniques either produce less uniform particles or particles of less desirable shapes or appearances, or also involve sizing or classification operations in which there are usually experienced losses of the speckles or after which recovered off-specification speckles have to be reprocessed.

In accordance with the present invention the above discussed disadvantages of prior art procedures are overcome and an improvement in the process for obtaining dentifrice speckles of substantially uniform shape and size is provided, which improvement comprises the steps of:

1. subjecting to high shear agitation a mixture of about 1 to 40% by weight speckling material comprising about 70 to 100 weight percent organic dentifrice binder and 0 to about 30 weight percent of functional and/or aesthetic dentifrice component(s) and about 60 to 99% by weight of a dispersing medium which has a normal boiling point at least 10° C. above the solidification point of said binder but which is below the normal boiling point of said binder material and which has a solidification point at least about 20° C. below the solidification point of said binder, said binder being substantially insoluble in said dispersing medium, agitation being applied at a temperature preferably at least about 10° C. above the solidification point of the binder but which is below the normal boiling point of the dispersing medium so that a homogeneous dispersion of substantially molten, usually hot, speckling material in liquid dispersing medium is obtained; and 2. cooling said dispersion under said high shear agitation to a temperature preferably at least about 20° C. below the solidification point of said binder to obtain solid dentifrice speckles having substantially uniform shape, preferably globular, and size in the range of about 0.5 to 1 mm. effective diameter, homogeneously dispersed in said dispersing medium, and optionally, separating the solid speckles from the liquid dispersing medium. The invention also includes the novel speckles prepared by this process and oral dentifrices, including powders, containing a uniform distribution of these speckles. The present improved process provides dentifrice materials of substantially uniform spherical shape and size in the range of 50 to 1,000 microns, avoiding the necessity of employing costly or tedious sieving or screening operations.

In the above description of the invention high shear agitation signifies turbulent flow agitation having a high energy input to the mixture being treated. For example, this can be from about 0.002 to about 0.2 horsepower per kilogram for mixture viscosities in the range of about 0.1 to 500 centipoises, at the operating temperatures. The mixers employed will usually have equivalent blade sizes of over seven centimeters in diameter, rotating at over 150 revolutions per minute. For example, the mixer blade or turbine may have a diameter of about 10 centimeters to 1 meter and may rotate at 150 to 4,000 r.p.m., e.g., at a lineal peripheral speed of about 5 to 100 meters per second.

By solidification point is meant the melting point or alternatively, the softening point or preferably, the hardening point in cases wherein the material does not have a sharp melting point.

By normal boiling point is meant the boiling point at atmospheric pressure (of course, the process may be modified to operate at subatmospheric or superatmospheric pressures, too.

In the process the dispersing medium is a liquid at the temperature to which the hot dispersion is cooled and the cooled solidified speckles are separated from the liquid dispersing medium by any conventional phase separation techniques, such as centrifugation, filtration or advantageously, settling and decantation. Desirably the dispersing medium is either water or a conventional liquid dentifrice vehicle of the type hereinafter described. In the latter embodiment of the process it may be convenient to incorporate all or a portion of the dispersing medium together with the speckles into the dentifrice rather than to effect a complete separation of the speckles from the dispersing medium first. Such can also be done with an aqueous medium.

In carrying out the present process the mixture subjected to high shear agitation preferably contains about 5 to 35%, especially about 10 to 25% by weight of speckling material, and about 65 to 95%, especially about 75 to 90%, by weight, dispersing medium.

While the binder can be used alone to provide speckling material it is generally preferable to incorporate in it conventional functional and/or aesthetic dentifrice component(s) in an amount up to about 30 weight percent based on the amount of speckling material. Preferably the concentration of functional and/or aesthetic component is about 0.01 to 25%. In an especially preferred embodiment of the invention the speckling material contains 0.01 to 10% by weight of a conventional dentifrice colorant, in addition to any other functional and/or aesthetic dentifrice components.

The speckling material, which, according to a preferred embodiment of the invention, contains conventional functional and/or aesthetic dentifrice components, is prepared in accord with conventional practice by melting the binder component thereof, admixing with it the functional and/or aesthetic dentifrice component(s), which can be a solid or liquid, and thoroughly agitating the resultant hot mixture to insure obtaining a solution or homogeneous dispersion of the functional and/or aesthetic component in the molten binder. Generally, mixing is accomplished in about 1 to 5 minutes. In a preferred embodiment of the invention the resultant molten speckling composition or material and the dispersing medium are, prior to being mixed, preheated to about the temperature at which high shear agitation is to be applied to them. Viscosity is at about 0.1 to 500, preferably 1 to 100 centipoises at the dispersion temperature.

The application of high shear agitation according to the invention can be effected in any heated mixer or blender capable of providing this type of agitation, for example a Petzholdt mixer. The agitation is preferably such that the liquid is in essentially or substantially radial flow, whereby good dispersion occurs. Generally, the homogeneous dispersion is obtained after 1 to 10 minutes, preferably 1 to 5 minutes of application of high shear agitation. Cooling of the hot agitated dispersion can be accomplished by means of a suitable conventional heat exchanger or advantageously, by dilution of the hot agitated dispersion with dispersing medium at or below the temperature to which it is desired to cool the dispersion to solidify the material of the speckles. Conveniently, 1 to 10-fold, preferably 1.5 to 4-fold and especially about 2.5-fold dilution of the hot dispersion with the cold dispersing medium is employed in cooling the agitated dispersion.

In preferred embodiments of the invention the organic binder employed has a solidification point of at least about 40° C. and a normal boiling point above about 200° C., preferably above 300° C., the elevated temperature at which dispersion is effected is between about 50° C. and 290° C., preferably 50° to 200° C., more preferably below about 100° C. and most preferably below 90° C., e.g., 50°–90° C. or 80° C. Preferably, the cool dispersing medium is at room temperature, i.e., 15°–25° C., generally about 20° C., and the temperature to which the dispersion is cooled is about room temperature. Cooling takes from 5 to 600 seconds, more preferably from 5 to 100 seconds.

The speckles of the invention are incorporated into oral dental pastes, gels or powders according to techniques which are conventional in the art of preparing speckled dentifrices. In general dentifrices having uniformly distributed speckles in accordance with the invention contain about 0.1 to 50% by weight or more speckles, preferably from 0.5 to 20%, and most preferably about 0.5 to 10%.

The sizes of the speckles prepared by the present process can be varied within the range of about 0.5 to 1 mm. by choice of dispersion conditions, i.e., use of a greater degree of high shear agitation within the given range and a higher temperature in the dispersion step results in smaller particle sizes. In general a speckle size in the range of about 0.2 to 0.6 mm. is particularly desirable. However, larger speckles up to 2 mm., can be made.

The binding agent employed in preparing the speckles according to the invention is any of a large number of physiologically acceptable organic compounds which are known to be compatible with functional and/or aesthetic dentifrice components so as to form a stable speckle or agglomerate therewith. Such products are insoluble in the dispersing medium. In particular, water-insoluble binders including one or more of thermoplastic materials, resins, gums, gels, paraffins, waxes, polymers, higher fatty acids and salts thereof, such as stearic acid, magnesium stearate, calcium stearate and the like, can be used.

A representative group of binders in accordance with this aspect of the invention are water-soluble, natural and synthetic materials classified as thermoplastic, i.e., materials that soften or melt and are made fluid when heated. Representative of these are polymers, particularly ethylenically unsaturated polymers such as polyethylene, polypropylene, polyvinyl chloride, polyvinyl acetate, copolymers of polyvinyl chloride and vinyl alcohol, vinyl acetate; vinylidene chloride; polymethacrylates, such as polymethyl methacrylate, polyethyl methacrylate, polyisopropyl methacrylate, polyisobutyl methacrylate; polyacrylates; polyamides, such as nylons; cellulosics such as acetates and butyrates; polycarbonates; coumaroneidene resins; paraffins and waxes, including natural waxes, such as carnauba, advantageously paraffins and waxes with melting points above 50° C.; and mixtures of the foregoing materials.

An advantage of the water-insoluble binders is maximum stability of the particles in the dentifrice, and these are particularly desirable when there are combined in the speckles water-soluble active ingredients, as well as water-insoluble components. In dispensing the dentifrice the particles do not streak but remain distinct and sparkling. Surprisingly, even though the particles are of macroscopically visible size, they can be of such sizes and characteristics as to be substantially inpalpable in the mouth during brushing.

Thermoplastic binding agents yield particularly advantageous results in preparing speckles by including in them a water-insolbule thermoplastic having a molecular weight between about 500 and about 20,000, preferably at least about 1,000. The hardness, expressed as tenths of mm. of needle penetration (100 grams/5 sec/25° C., ASTM D1321), of preferred materials in this class is typically between about 1 and 15, although harder grades can be used if not objectionable in the final toothpaste. The following table lists the properties of thermoplastic binding agents representative of this class.

glyceryl tristearate; glyceryl tripalmitate; glyceryl trilaurate; glyceryl tridocosylate; glyceryl distearate; glyceryl dimyristate;

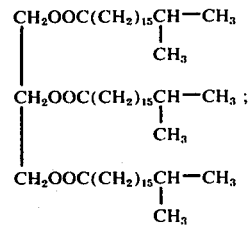

glycerol triesterified with an equimolar mixture of lauric and stearic acids; glyceryl tricocate; glyceryl

TABLE

| Resin | A.M.W.[1] | S.p.[2] Approx. | Hardness[3] | S.G.[4] | A.V.[5](Cps.) | Temp.(° C.) |
|---|---|---|---|---|---|---|
| Polyethylene[6] | 2,000 | 105° C. | 3.5 | 0.92 | 200 | 140 |
| Polyethylene[6] | 2,200 | 107° C. | 3.0 | 0.92 | 220 | 140 |
| Polyethylene[6] | 3,500 | 116° C. | 1.0 | 0.93 | 350 | 140 |
| Polyethylene[6] | 1,500 | 102° C. | 7.5 | 0.91 | 145 | 140 |
| Polyethylene[6] | 1,100 | 195° C. | 80.0 | 0.89 | 40 | 140 |
| Polyethylene[6] | 2,000 | 96° C. | 9.5 | 0.91 | 230 | 140 |
| Polyethylene[6] | 3,500 | 204° C. | 7.0 | 0.92 | 500 | 140 |
| Oxidized polyethylene[7] | 1,800 | 104° C. | 4.0 | 0.94 | 320. | 125 |
| Oxidized polyethylene[7] | 3,000 | 106° C. | 3.0 | 0.94 | 1,200 | 125 |
| Polyamide[8] | 6,000–9,000 | 110° C. | 4.0 | 0.98 | 2,200 | 150 |
| Polyamide[8] | 6,000–9,000 | 95° C. | 15.0 | 0.98 | 1,100 | 150 |

[1] = Average Molecular Weight
[2] = Softening Point (Approx.) ASTM E-28
[3] = 0.1 mm. Needle Penetration ASTM D-1321 (100 grams/5 sec./25° C.)
[4] = Specific Gravity
[5] = Average Viscosity, Centipoises
[6] = Available from Allied Chemical Company under the trademark A-C polyethylene, grades 6, 6A, 7, 7A, 8, 8A, 615, 617, 617A, G-201 and 400
[7] = Available from Eastman Chemical Products, Kingsport, Tennessee under the trademark EPOLENE. These materials are emulsifiable and have both an acid value and saponification number of 9-10. Similar materials are available from Allied Chemical Company under the trademark A-C polyethylene, grades 656, 629, 655 and 680.
[8] = Produced from ethylene diamine in accordance with U.S. patent number 2,370,413. Available from the Chemical Division of General Mills Co., Kankakee, Illinois, under the trademark Versamid, grades 930, 940 and 950.

A preferred class of water insoluble binders includes the lower alkylene glycol and polyol di-higher esters, particularly the ethylene glycol diesters and the glyceryl di- and tri-esters of higher fatty acids of 10 to 22 carbon atoms, preferably of 12 to 18 carbon atoms and wherein the fatty acids are preferably saturated. These esters are normally soft, fatty substances having particularly suitable melting points in the range of about 45° to 80° C. Typical representative examples of this preferred class of binding agents include the following: tri-hydrogenated cocate; ethylene glycol distearate; ethylene glycol dilaurate; ethylene glycol dipalmitate; ethylene glycol dicocate; and ethylene glycol di-hydrogenated cocate. An especially good result is obtained using the readily available glyceryl tristearate (m.p. 71.6° C.). "Cocate" is coconut acid ester.

The dispersing medium of the invention is any acceptable inorganic or organic liquid whose normal boiling point and solidification point have the above-described relationship to the solidification and normal boiling points of the organic binders. Preferably, as stated above, the dispersing medium is water, an aqueous solution or other conventional liquid dentifrice vehicle such as glycerol, aqueous sorbitol solution, propylene glycol, polyethylene glycol 400, mannitol or similar polyhydric lower alcohol of 2 to 6 carbon atoms. Most preferred is water, preferably deionized, especially for glyceryl tristearate speckles.

The speckles of this invention are preferably employed in oral dental pastes, gels or creams, including transparent, translucent and opaque pastes or creams, but also can be employed in oral dental powders. The following description of the functional and/or aesthetic components of oral dentifrices is directed to creams, gels and pastes but it will be understood by those skilled in the art that suitable powders can be made which differ from the creams, gels, etc., primarily in being substantially devoid of liquid dentifrice vehicles, water and thickening agents. It will also be understood that the concentrations given below for conventional functional and/or aesthetic dentifrice components are total concentrations for the component in the dentifrice, including the amount which may be present in the speckles. Normally, these will contain 10 to 100%, preferably 50 to 100% of such added materials when such are in the speckles.

An important functional component of the dentifrice is an anticaries agent. Examples of dentally effective fluorine-containing substances include inorganic and organic fluorine-containing materials, preferably fluoride salts. Suitable inorganic fluorides include sodium monofluorophosphate, sodium fluoride, stannous fluoride, potassium fluoride, indium fluoride, potassium stannous fluoride ($SnF_2$-KF), potassium fluorozirconate, sodium hexafluorostannate and stannous chlorofluoride. Organic fluorine compounds such as amine hydrofluorides may be used, for example, lauryl amine hydrofluoride and cetylpyridinium fluoride.

The function of a fluorine-containing ingredient is to provide a beneficial effect on the care and hygiene of the teeth by reducing the solubility of enamel tissue in acid environment and to protect the teeth against decay. The foregoing fluorine materials, which dissociate or release fluorine-containing ions, suitably may be present in an effective but non-toxic amount, usually within the range of about 0.01 to 1% by weight of the water-soluble fluorine content thereof.

Antimocrobial agents are incorporated into oral dentifrice formulations to promote oral hygiene, and generally may be effective by reducing dental plaque, improving gingival conditions, inhibiting the formation of dental calculus, or reducing or modifying the number of types of micro organisms. Representative antimicrobial agents include cationics and particularly the biguanide materials including: $N^1$-(4- chlorobenzyl )-$N^5$-(2,4-dichlorobenzyl) biguanide; p-chlorophenyl biguanide; 4-chlorobenzhydrylguanylurea; N-3-lauroxypropyl-$N^5$-p-chlorobenzylbiguanide; 1-(lauryldimethylammonium)8-(p-chlorobenzyldimethylammonium) octane dichloride; 5,6-dichloroguanidinobenzimidazole; $N^1$-p-chlorophenyl-$N^5$-laurylbiguanide; 1,6-di-p-chlorophenyl biguanidohexane; 1,6-bis(2-ethylhexyl biguanido) hexane; 5-amino-1,3-bis(2-ethylhexyl)-5-methylhexahydropyrimidine; and their non-toxic acid addition salts, such as chlorides, bromides and methosulfates.

Additional antimicrobial agents useful in the invention are quaternary ammonium carbamate, thiocarbamate, dithiocarbamate and carbamide compounds such as those disclosed in U.S. Pat. No. 3,621,048; the dichloro-2-guanidino benzimidazoles disclosed in U.S. Pat. No. 3,523,154; and the imidazoles of U.S. Pat. No. 3,497,591. The foregoing antimicrobial agents are generally employed in concentrations of about 0.01 to 5 weight percent, more often at 0.1 to 2% in dentrifice formulations.

Other functional ingredients which may be used in similar suitable amounts include ammoniated materials such as urea and diammoniums phosphate; water-soluble chlorophyllins; vitamins such as Vitamins $B_6$, $B_{12}$ complex or Vitamin E; desensitizing materials such as strontium salts, e.g., strontium salts, e.g., strontium chloride; antibiotics such as tyrothricin, vancomycin, tylosin, demycosin and the macrolides of U.S. Pat. No. 3,342,687; protaglandins; enzymes such as dextranase and enzyme products having a neutral protease activity of at least about 700,000 to 2 million casein units of activity per gram and derived from B. Subtilis; phenols; hexachlorophene; optical brighteners such as 4-methyl-7-hydroxy or 4-methyl-7-diethylamine coumarin; astringents such as zinc chloride, zinc sulphate, aluminum lactate, etc., and preservatives such as sodium benzoate.

Among the active ingredients are included materials which tend to freshen the breath such as flavoring oils, e.g., peppermint oil, spearmint, anise, menthol, and others which are well known, and sweetening agents such as saccharine and sorbitol (which has a sweetening effect). Generally, a flavoring agent is present in a concentration of about 0.1 to 10%, preferably 0.2 to 3% of the dentifrice.

Organic surface-active agents are used in oral dentifrice compositions to assist in achieving thorough and complete dispersion of the composition throughout the oral cavity and to render them more cosmetically acceptable. The organic surface-active material may be anionic, nonionic, ampholytic, or cationic in nature, and it is preferred to employ as the surface-active agent a detersive material which imparts to the composition detersive and foaming properties. Preferably anionic surface-active agents are used. Such compounds may include long chain fatty or poly-lower alkoxy groups plus hydrophilic radicals. They will usually be in the form of salts, especially water soluble salts of alkali or alkaline earth metals. Among the useful anionic detergents may be mentioned the higher fatty acid monoglyceride monosulfates, such as the sodium salts of the monosulfated monoglycerides of hydrogenated coconut oil fatty acid; higher alkyl sulfates, such as sodium lauryl sulfate; higher alkyl aryl sulfonates, such as sodium linear dodecyl benzene sulfonate; higher olefin sulfonates, such as sodium higher olefin sulfonate in which the olefin group is 12 to 21 carbon atoms; higher alkyl potassium sulfoacetates; higher fatty acid esters of 1,2-dihydroxypropane sulfonates, as magnesium salts; the substantially saturated higher aliphatic acyl amides of lower aliphatic aminocarboxylic acid alkali metal salts, such as those having 12 to 16 carbon atoms in the fatty acyl radicals; higher alkyl poly-lower alkoxy (of 10 to 100 alkoxies) sodium sulfates; higher fatty acid sodium and potassium soaps of coconut oil and tallow, and the like. As is noted, most frequently the detergents are sulfated or sulfonated compounds, known as sulfuric reaction products. Examples of useful anionic amides which may be employed are N-lauroyl sarcosine and the sodium, potassium and ethanolamine salts of N-lauroyl-, N-myristoyl- and N-palmitoyl sarcosines. In the above descriptions, "higher" refers to chain lengths of 12 to 22 carbon atoms, preferably of 12 to 18 carbon atoms and most preferably of 12 to 16 carbon atoms. Lower means of 2 to 4 carbon atoms, preferably 2 to 3 carbon atoms and most preferably, two carbon atoms. Additional descriptions of such compounds may be found in the text, Surface Active Agents, Vol. II (1958), by Schwartz, Perry and Berch.

The nonionic detergents include those containing chains of lower alkylene oxide, e.g., ethylene oxide, propylene oxide, in which there are present from 10 to 100 or more moles of lower alkylene oxide. Among such materials are the block co-polymers of ethylene oxide, propylene oxide and propylene glycol, sold as Pluronics; the alkyl phenyl polyethoxy ethanols, sold as Igepals; the mixed co-polymers of ethylene oxide and propylene oxide, sold as Ucons; and various other well known nonionics derived from fatty alcohols or acids and polyethylene oxide. The amphoteric or ampholytic agents include quaternized imidazole derivatives, such as "Miranols", e.g., Miranol C₂M; and among the suitable cationic germicidal detergents are such as diisobutylphenoxyethoxyethyl dimethyl benzyl ammonium chloride; benzyl dimethyl stearyl ammonium chloride; and tertiary amines having a higher fatty alkyl group and two polyoxyethylene groups attached to the nitrogen thereof. Of course, reference to the mentioned text and to *Detergents and Emulsifiers* 1969 *Annual*, by McCutcheon, will indicate to one of skill in the art various other suitable surface active detergent and foaming constituents which may be employed in these compositions. Mixtures thereof may be used to adjust properties to obtain the most desired effect. However, in making such mixtures it will generally be desired to avoid using both anionics and cationics together.

The detergents constitute from 0.5 to 5% of the dentifrice in most cases, although in some instances slightly larger proportions of detergent may be utilized. Rarely, however, will this be greater than 10%. In preferred embodiments of the invention, the detergent content may be decreased to about 1 to 3%. The most preferable detergents utilized are sodium lauryl sulfate or myristyl or palmityl sulfates and sodium N-lauroyl sarcoside, or the corresponding myristoyl or palmitoyl compounds. Also useful are formulations in which mixtures of these two different types of detersive materials are employed. When nonionics are utilized, they will normally be from 0.1 to 3% of the product, preferably from 0.5 to 2% thereof. The amphoterics and cationics can normally be present in proportions less than 2%, preferably less than 1%, but generally more than 0.1%, if employed.

Polishing agents are particularly important ingredients in dentifrices performing an important mechanical cleaning function. The polishing agents are usually finely divided water insoluble powdered materials of particle sizes such that they pass a 140 mesh screen, U.S. Standard Sieve Series. Preferably, they are from 1 to 40 microns, most preferably from 2 to 20 microns in particle sizes, with distribution of particles sizes being normal over the range.

Among the polishing agents that are useful in the preparation of dentifrices may be mentioned dicalcium phosphate, tricalcium phosphate, insoluble sodium metaphosphate, crystalline silica, colloidal silica, complex aluminosilicates, aluminum hydroxide (including alumina trihydrate), magnesium phosphate, magnesium carbonate, calcium carbonate, calcium pyrophosphate, bentonite, talc, calcium silicate, calcium aluminate, aluminum oxide, aluminum silicate, and silica xerogels. In the cases of many of such ionic polishing agents corresponding to alkali metal or alkaline earth metal salts, respectively, may be employed. The above listing of polishing agents, and other listings of other constituents of the dentifrice composition to be given in the present specification are not intended to be exhaustive and therefore, for other materials of these types reference should be made to a standard handbook, such as *Cosmetics:Science and Technology*, by Sagarin, 2nd printing, 1963, published by Interscience Publishers, Inc. Most of the polishing agents mentioned are most useful in the preparation of opaque dentifrices but some of them, such as the colloidal silicas, especially the silica xerogels and complex sodium aluminosilicates, may be utilized in the manufacture of transparent or clear gel dentifrices, because their indexes of refraction approximate those of the rest of the dentifrice constituents in an appropriate vehicle. Of course, the speckled appearances caused by the regular speckles of this invention are most visually effective in clear gel or other clear dental preparations, including clear gelled mouthwashes and other oral products.

The content of polishing agent in the final dentifrice product is variable, generally being greater for the opaque than for the translucent or transparent dental gels. For example, in the manufacture of commercially acceptable opaque form-retaining extrudible dental creams there usually will be present 20 to 75% of polishing agent, e.g., dicalcium phosphate, but in the manufacture of clear dental gels, also form-retaining and extrudable, the content of polishing agent is typically from 5 to 40%. The preferred proportions of such constituents are 40 to 60% and 10 to 30%, respectively. In the case of the polishing agent for opaque products, a preferred composition includes hydrated dicalcium phosphate and anhydrous dicalcium phosphate, with the latter being present to the extent of about 5 to 20% of the total dicalcium phosphate content. With respect to the transparent or translucent dental gels, either sodium aluminosilicate complex or silica xerogel can usually be employed, separately, although mixtures thereof may find special advantages in some products where the desired polishing properties may be so regulated. It will be seen that the polishing agents utilized in accordance with the invention are normally water insoluble inorganic metal oxides, hydroxides, salts or hydrates but water insoluble organic compounds may also be employed in substitution thereof, although usually for only minor proportions of the total polishing agent. For example, polyacrylamides, polymethyl methacrylates polyesters and nylons of sufficient hardnesses may be utilized.

Of the water insoluble polishing agents, most are well known chemical compounds. The complex aluminosilicate salts, which appear to contain interbonded silica and alumina having Al-O-Si bonds, are described by Tamele, in "Chemistry of the Surface and the Activity of Aluminum-Silica Cracking Catalysts", appearing in *Discussions of the Faraday Society*, No. 8, pages 270–279 (1950), particularly at page 273, FIG. 1, Curve 3, and in the article by Milliken et al., entitled "The Chemical Characteristics and Structure of Cracking Catalysts", in Discussions of Faraday Society, No. 8, 279–290 (1950), particularly in the sentence bridging pages 284 and 285. The colloidal silicas used are silica xerogels. Typically, they contain up to about 20% of water, have a refractive index of 1.44 to 1.47 and a loose bulk density of about 0.07 to 0.12 g./c. cm. and are of particle sizes of 1 to 20 microns. Appropriate xerogels have been marketed under the trademarks Syloid 63 and Syloid 74.

Among important aesthetic components of dentifrice compositions are colorants or coloring agents, including white, which may be any dye or pigment which is physiologically acceptable. Of course, if the "binder" is of desired color or whiteness a colorant may be omitted. Usually solid colorants for dentifrices are employed in finely divided form, for example, as particles having an average particle size of less than 2 microns and advantageously, than 1 micron, with the maximum particle size not exceeding 5 or 10 microns. Inorganic pigments which can be used as colorants include titanium dioxide, tricalcium phosphate, calcium carbonate, and calcium sulfate and colored pigments, too, are useful, e.g., iron oxide, ultramarine blue, ochre, carmine and phthalocyanine pigments. Among organic dyes it is particularly advantageous to employ those certified for food use, such as Color Index 75,120, 75,130, 75,810, 69,800, 42,051, 75,470, 1,758, 14,720, 16,185, 15,985, 15,980, 75,300, 19,140 and 44,270. Oil soluble dyes are usually preferred. The metallic lakes of such dyes are useful as colorants for dentifrices. Other dyestuffs which can be used include natural dyes such as oil soluble chlorophyll (Color Index 75,810) and carotene (Color Index 75,130). Typical proprietary coloring agents useful in coloring dentifrices also include Pigment Red 5 (Color Index 15,490), Pigmosol Carmine G, Pigmosol Green GN, Pigmosol Blue B, Irgalite Carmine FB, Viscofil Green 2GL and Fenalac Blue B. In addition to the foregoing solid colorants, liquid colorants such as azulin can also be used. The pigment should be oil dispersible or the dye oil soluble if an oily, greasy, fatty or waxy binder or base is used, so as to have its greatest coloring effect.

As was mentioned, the dentifrice may be a powder but is preferably a gel or paste. The gels or pastes are made cream-like and extrudible from a collapsible tube, such as an aluminum, lead or plastic tube, by the presence of a vehicle containing a liquid component, i.e., water and the organic liquid dentifrice vehicle discussed above, and a solid component, i.e., one or more gelling agents such as natural and synthetic gums and gum-like materials, e.g. Irish Moss, tragacanth, alkali metal carboxylmethyl cellulose, hydroxymethyl carboxyethyl cellulose, polyvinyl pyrrolidone, starch, water-soluble hydrophilic colloidal carboxyvinyl polymers such as those sold under the trademark Carbopols 934 and 940, and silica aerogels. The concentration of organic liquid vehicle in extrudible dentifrices ranges from about 10 to 90 weight percent with a concentration of 10 to 35 weight percent being a typical concentration for the liquid organic vehicle in an opaque paste and a concentration of from about 40 to 90% by weight being a typical concentration for a liquid organic vehicle in a clear gel dentifrice. The water content of the gel or paste dentifrice, including water introduced with alcoholic organic vehicles, or other constituents, such as surface active agents, often is greater for opaque pastes, gels or creams than for clear products. For example, the water contents of opaque pastes usually range from about 5 to 50% by weight while that for clear gel dentifrices is from about 0 to 30% by weight. The concentration of the gelling agent is usually about 0.2 to 10% by weight of the dentifrice, e.g., 0.5%.

The present invention includes incorporation of one or several of the aforementioned functional and/or aesthetic dentifrice components in the speckles, preferably one selected from the group consisting of anticaries agents, antimicrobial agents, colorants, surface active agents, enzymes, astringents, flavors, sweeteners, optical brightening agents and polishing agents.

In the separate speckles such components may be kept in more stable form than when distributed throughout the dental preparation.

The following examples illustrate the invention but do not limit it. All parts, percentages and proportions are by weight unless otherwise noted and temperatures are in °C.

EXAMPLE 1

| | Parts |
|---|---|
| Glyceryl tristearate | 99.5 |
| Oil soluble chlorophyll | |

EXAMPLE 1-continued

| | Parts |
|---|---|
| (Color Index 75810) | 0.5 |

The glyceryl tristearate is melted and agitated with the chlorophyll. The resultant molten green mass is heaed to about 80° and admixed with 300 parts of deionized water which has been preheated to 80°. The resultant aqueous mass is subjected to high shear agitation at about 80° in a vertical shaft mixer having a large diameter mixing blade for two minutes at 300 r.p.m. until the mixture becomes homogeneous. The mixer and blade diameters are about 50 cm. and the mixer is 1 meter tall, with the blade thickness of 2 cm. at a height of 40 cm. above the base. The mix is cooled to room temperature by dilution with an additional 600 parts of deionized water at 10° C. The agitation is discontinued and after 5 minutes standing the aqueous dispersion of green spherical particles is filtered to recover about a 90% yield of green speckles characterized by substantially uniform spherical shape and uniform size. The moist green speckles are reserved for uniform distribution in a oral dentifrice paste at a concentration of about 0.5% (by weight) as described in Example VI below. They are spheres with about 90% thereof of 0.4 to 0.6 mm. dia.

When the proportion of chlorophyll is decreased to as little as 0.05% the decided green coloration is still noted. Usually concentrations in excess of 5% will not be employed because they tend to make the speckles appear black at such higher concentrations. Separation from the aqueus medium may be also by centrifuging, settling and decantation or simple screening. Subsequently, the particles may be dried in an air blast or current. If not dried, they may be added to a dental product together with the medium employed, which is a dentifrice component.

EXAMPLE 2

| | | Parts |
|---|---|---|
| Part A | | |
| | Glyceryl tristearate | 99 |
| | Carotene (Color Index 75,130) | 1 |

The procedure of Example 1 is repeated substantially as described except that carotene is used in place of chlorophyll, the solid speckles are not recovered from the cooled aqueous product dispersion, and the described mixer is set at the same speed setting for one minute at 300 r.p.m., providing a high shear agitation corresponding to an energy input in horsepower per kg, range previously described. The resultant yellow speckles of the aqueous dispersion are characterized by substantially uniform rounded shape. More than 90% of the speckles are of a substantially uniform size of 0.45 mm. ±33%, effective diameter.

Part B

The procedure of Part A above is repeated, employing the high speed of the mixer, providing a high shear agitation for 3 minutes at 300 r.p.m. at the same viscosity as in Part A. The resultant aqueous dispersion of attractive yellow speckles is of a substantially uniform spherical shape and of a substantially uniform size of 0.34 mm. ±47%.

When the same or other equivalent high shear mixers are employed to produce the high shear agitation at blade speeds of about 5 to 100 meters/second, good dispersions are made and globular particles are produced. This is also the case when the temperature is varied from 50° to 90° C. but preferably it is held in the 60° to 80° C. range to melt and disperse the binder. Horsepower inputs per kg. may be from 0.002 to 0.2.

The following examples, 3 and 4 illustrate the preparation of speckles containing both aesthetic and functional dentifrice components.

EXAMPLE 3

|  | Parts |
| --- | --- |
| Glyceryl tristearate | 79 |
| Zirconium silicate | 20 |
| Chlorophyll (as in Example 1) | 1 |

The procedure of Example 1 is repeated substantially as described to produce an aqueous dispersion of solid speckles from the above ingredients. The resulant green speckles containing both an aesthetic dentifrice component, chlorophyll colorant, and a functional dentifrice agent, zirconium silicate polishing agent, are characterized by substantial uniformity in size, about 0.8 mm. diameter and spherical shape. Similar products result when paraffin wax, polyethylene, glyceryl tripalmitate, ethylene glycol distearate, glyceryl distearate, nylons, or polyvinyl chloride is employed, with heating being to 200° C., above the melting point thereof and below the boiling point of the dispersing medium employed, with quick cooling, in from 5 to 60 seconds, to a temperature below the solidification point.

EXAMPLE 4

|  | Parts |
| --- | --- |
| Glyceryl tristearate | 79 |
| Menthol | 20 |
| Chlorophyll (as in Example 1) | 1 |

The procedure of Example 1 is repeated in preparing an aqueous dispersion of solid speckles from the above listed materials. The resultant dispersed green speckles, which contain two different aesthetic dentifrice components, chlorophyll colorant and menthol flavor, are characterized by substantial uniformity in size and spherical shape.

EXAMPLE 5

|  | Parts |
| --- | --- |
| Polyethylene (softening point 130°) | 99.6 |
| Chlorophyll (as in Example 1) | 0.4 |

In a vessel equipped with a Lightnin' mixer the polyethylene is melted, heated to 140° C. and admixed with the chlorophyll. The hot, colored polyethylene is mixed with 300 parts of glycerol, which has been preheated at 140° C. The resultant mixture is subjected to high shear agitation as in Example 1 to obtain a homogeneous dispersion of the molten colored polyethylene in droplet or globular form in the glycerol. The hot dispersion is cooled to room temperature under high shear agitation by addition of 1,000 parts of glycerol at 10°, plus utilizing cooling means (cooling water jacket on the vessel. On completion of cooling to 30° C. the agitation is discontinued and the dispersion is allowed to stand for ten minutes and 1,100 parts of glycerol are decanted from the dispersion. The resultant concentrated glycerol dispersion of colored polyethylene speckles is mixed with an oral dental gel to provide uniformly green speckled dentifrice wherein the speckles are characterized by substantially uniform spherical shape and size, about 0.5 mm. diameter ±20%. In other operations the diameters are varied from 0.1 to 0.8 mm. selectively by modifications of the temperature and stirring shear conditions. Also, the speckles are included in gel mouthwashes as well as in conventional gelled tooth cleaning compositions and in some cases the base gel is lightly colored with the same or different colorant at a lower concentration, e.g., 0.001 to 0.02%. Some clear dentifrices in which the speckles are incorporated are those of U.S. Pat. No. 3,711,604, Exs. 5–11.

EXAMPLE 6

|  | Parts |
| --- | --- |
| Glycerol (99.3%) | 19.8 |
| Sodium carboxymethyl cellulose | 8.5 |
| Sodium saccharin | 0.2 |
| Sodium benzoate | 0.5 |
| Tetrasodium pyrophosphate | 0.3 |
| Water | 19.9 |
| Magnesium phosphate | 0.2 |
| Calcium carbonate | 5.0 |
| Dicalcium phosphate dihydrate | 46.3 |
| Sodium N-lauroyl sarcosinate | 5.7 |
| Mint flavor | 0.8 |
| Glyceryl tristearate | 0.5 |
| Chlorophyll (as in Example 1) | 0.003 |

The green speckled product made from the chlorophyll and glyceryl tristearate dispersing agent in the manner of Example 1, is uniformly distributed at a concentration of 0.5 weight percent in the balance of the product, an opaque dentifrice, according to a conventional blending technique, to provide an attractive, green speckled opaque paste of the composition set forth above. Corresponding visually clear dentifrices are also made.

Although the paste is opaque the speckles are visible, especially on the outer portions of the extruded ribbon. The product cleans the teeth well and has a breath freshening flavor, while being of distinctive and attractive appearance. In other variations of the formula the speckles contain other colorants, including organic dyes and pigments and inorganic pigments which are oil dispersible. Additional adjuvants suchh as germicides, e.g., hexachlorophene; polishing agents, e.g., calcium carbonate; surface active agents, e.g., sodium N-lauroyl sarcoside; gums, e.g., sodium carboxymethyl cellulose; and oxidants, e.g., sodium perborate, are also included in the speckles to the extent of about 0.1 to 2% each. They are of improved stabilities and noticeable activities in use. Clear dentifrices are also so improved.

The invention has been described with respect to examples and illustrations but is not to be limited to these because one of skill in the art with the present specification before him will be able to utilize substitutes and equivalents without departing from the spirit of the invention or the scope of the claims.

What is claimed is:

1. A process for making dentifrice speckles of substantially uniform shape and size which comprises:

A. agitating a heated mixture of a speckling material and a dispersing liquid for said speckling material, said speckling material containing a dentifrice component and a binder for such component, at a temperature at which the binder is liquid, to produce a homogeneous dispersion in the dispersing liquid of individual droplets of said speckling material of sizes in the range of about 0.05 to 1 mm. effective diameter; said mixture being of about
   I. 1 to 40% by weight of such speckling material, which is
      a. about 75 to 99.9% by weight of a normally solid water insoluble organic dentifrice binder selected from the group consisting of thermoplastic resins, gums, gels, paraffins, waxes, polymers, higher fatty acids, higher fatty acid salts, lower alkylene glycol diesters, glyceryl diesters and glyceryl triesters; and
      b. about 0.01 to 25% by weight of a dentifrice component selected from the group consisting of fluorine-containing anti-caries agents, polishing agents, antimicrobial agents, ammoniating agents, vitamins, desensitizing agents, enzymes, optical brighteners, astringents, perservatives, flavoring agents and colorants; and
   II. about 60 to 99% by weight of a dispersing liquid which has a normal boiling point which is at least 10° C. above the solidification point of said binder and below the normal boiling point of said binder and which has a solidification point at least 20° C. below the solidification point of the binder, in which dispersing liquid the binder is substantially insoluble, said dispersing liquid being selected from the group consisting of water and aqueous solutions of lower polyhydric alcohols of 2 to 6 carbon atoms; and
B. cooling such mixture of speckling material and dispersing liquid, while containing agitation thereof, to a temperature below the solidification point of said binder, at which temperature the dispersing liquid remains liquid, to obtain solid dentifrice speckles of the binder and dentifrice component in the dispersing liquid, having substantially uniform shape and sizes in the range of about 0.05 to 1 mm. effective diameter, homogeneously dispersed in said dispersing liquid.

2. A process according to claim 1 wherein the heated mixture of speckling material and dispersing liquid is made by separately pre-heating speckling material and dispersing liquid and mixing them together, the heated mixture contains about 5 to 35% of speckling material and 65 to 95% of dispersing liquid, shear agitation is applied at the elevated temperature and the temprature to which the dispersing is cooled is at least about 20° C. below the solidification point of the binder.

3. A process according to claim 2 wherein the solidification temperature of the binder is at least 40° C., the normal boiling point of the binder is above the elevated temperature at which agitation is effected before cooling, the dispersing liquid is a liquid at room temperature, the normal boiling point of the dispersing liquid is below about 300° C., the temperature at which the dispersion is effected is between about 50° and 190° C., the temperature to which the dispersion is cooled is about room temperature, the shear agitation is turbulent flow agitation at 0.002 to 0.2 horsepower per kilogram of mixture and the viscosity of the mixture during agitation at elevated temperature is in the range of 0.1 to 500 centipoises.

4. A process according to claim 3 wherein the heated mixture contains about 10 to 25% of speckling material and 75 to 90% of dispersing liquid, the dispersing liquid is water, the elevated temperature at which dispersion is effected is below 100° C. and the solid speckles are separated from the dispersing liquid.

5. A process according to claim 4 whether the shear agitation is equivlent to that of a mixer having a blade size of over seven centimeters in diameter which is rotating at over 150 revolutions per minute, the speckling material contains about 0.01 to 2% of colorant which is mixed with molten binder before the speckling material is mixed with the dispersing liquid and the binder is glyceryl tristearate.

6. A process according to claim 5 wherein the colorant is present in the speckling material at a concentration of about 1% based on the weight of the speckling material and the agitation is effected by means of a mixer withh a blade having a linear peripheral speed of about 5 to 100 meters per second.

7. A process according to claim 6 wherein the colorant is oil soluble chlorphyll.

8. A process according to claim 7 wherein the speckling material contains about 20% of zirconium silicate as a polishing agent.

9. A process according to claim 8 wherein the speckling material contains about 20% of menthol as a flavoring agent.

* * * * *

UNITED STATES PATENT AND TRADEMARK OFFICE
CERTIFICATE OF CORRECTION

PATENT NO. : 4,003,971
DATED : January 18, 1977
INVENTOR(S) : Giuseppe Mannara

It is certified that error appears in the above-identified patent and that said Letters Patent are hereby corrected as shown below:

Col. 1, line 51 cancel "ticular" and insert --ticulate--;

Col. 5, line 7 cancel "inpalpable" and insert --impalpable--;

Col. 5, line 10 cancel "insolbule" and insert --insoluble--;

Correct the disclosure following Col. 5, line 55 by removing the disclosure printed at Col. 6, lines 1-19 therefrom and inserting same following Col. 5, line 55;

Col. 7, line 61 cancel "strontium salts, e.g.,";

Col. 14, line 50 cancel "suchh" and insert --such--;

Col. 15, line 38 cancel "containing" and insert --continuing--;

Col. 16, line 5 cancel "dispersing" and insert --dispersion--;

Col. 16, line 28 cancel "equivlent" and insert --equivalent--;

Col. 16, line 39 cancel "withh" and insert --with--;

Col. 16, line 42 cancel "chlorphyll" and insert --chlorophyll--;

Signed and Sealed this

Fourteenth Day of February 1978

[SEAL]

Attest:

RUTH C. MASON
Attesting Officer

LUTRELLE F. PARKER
Acting Commissioner of Patents and Trademarks